United States Patent
Lin

(10) Patent No.: US 7,601,437 B2
(45) Date of Patent: *Oct. 13, 2009

(54) ORGANOMETALLIC COMPOUNDS AND DISPLAY DEVICE EMPLOYING THE SAME

(75) Inventor: Cheng-Hung Lin, Hemei Township, Changhua County (TW)

(73) Assignee: AU Optronics Corp., Hsinchu (TW)

( * ) Notice: Subject to any disclaimer, the term of this patent is extended or adjusted under 35 U.S.C. 154(b) by 696 days.

This patent is subject to a terminal disclaimer.

(21) Appl. No.: 11/045,995

(22) Filed: Jan. 28, 2005

(65) Prior Publication Data

US 2006/0078758 A1    Apr. 13, 2006

(30) Foreign Application Priority Data

Oct. 7, 2004    (TW) ................. 93130362 A

(51) Int. Cl.
*H01L 51/54*    (2006.01)
*C09K 11/06*    (2006.01)

(52) U.S. Cl. .............. 428/690; 428/917; 313/504; 257/E51.044; 548/101; 548/103; 548/110

(58) Field of Classification Search ............ None
See application file for complete search history.

(56) References Cited

U.S. PATENT DOCUMENTS

| | | | |
|---|---|---|---|
| 5,484,922 A * | 1/1996 | Moore et al. | 546/7 |
| 6,465,115 B2 | 10/2002 | Shi et al. | 428/690 |
| 6,687,266 B1 * | 2/2004 | Ma et al. | 372/7 |
| 6,936,716 B1 * | 8/2005 | Lin | 546/2 |
| 2002/0024293 A1 | 2/2002 | Igarashi et al. | 313/483 |
| 2002/0182441 A1 | 12/2002 | Lamansky et al. | 428/690 |
| 2003/0072964 A1 | 4/2003 | Kwong et al. | 428/690 |
| 2003/0116788 A1 | 6/2003 | Sakakibara et al. | 257/200 |
| 2004/0102632 A1 | 5/2004 | Thompson et al. | 546/2 |
| 2006/0008670 A1 * | 1/2006 | Lin et al. | 428/690 |
| 2008/0038586 A1 | 2/2008 | Nishizeki et al. | |

FOREIGN PATENT DOCUMENTS

| JP | 2006054236 | 2/2006 |
|---|---|---|
| WO | WO2006008976 | 1/2006 |

OTHER PUBLICATIONS

Li et al., "Synthesis and characterization of cyclometalated Ir(III) complexes with pyrazolyl ancillary ligands", Polyhedron, vol. 23, Issues 2-3, pp. 419-428, Jan. 22, 2004.*

Taiwan Office Action dated Feb. 9, 2006.
English Translation of JP Office Action mailed Aug. 7, 2008.
English Abstract of JP2006054236 (Feb. 2006).
English Abstract of WO2006008976 (Jan. 2006).
International Search Report for PCT/JP2005/012584 (dated Oct. 25, 2005).

* cited by examiner

*Primary Examiner*—Marie R. Yamnitzky
(74) *Attorney, Agent, or Firm*—Thomas, Kayden, Horstemeyer & Risley

(57) ABSTRACT

Organometalic compounds, having formula I

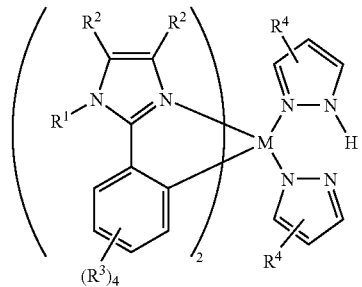

or formula (II)

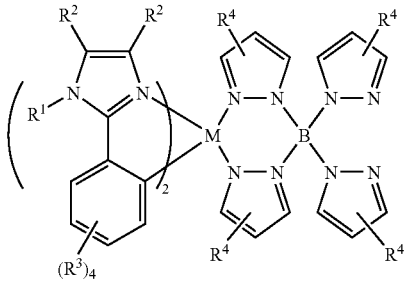

can serve as host materials for an organic electroluminescent device. Furthermore, the organometallic compounds can also serve as green phosphorescent dopant material for display devices.

10 Claims, 1 Drawing Sheet

ORGANOMETALLIC COMPOUNDS AND DISPLAY DEVICE EMPLOYING THE SAME

BACKGROUND

The invention relates to an organometallic compound and, more particularly, to an organometallic compound serving as electroluminescent material for an organic electroluminescent display device.

Recently, with the development and wide application of electronic products, such as mobile phones, PDA, and notebook computers, there has been increasing demand for flat display elements which consume less electric power and occupy less space. Organic electroluminescent devices are self-emitting and highly luminous, with wider viewing angle, faster response speed, and simpler fabrication, making them the industry display of choice.

Generally, an OLED is composed of a light-emitting layer sandwiched between a pair of electrodes. When an electric field is applied to the electrodes, the cathode injects electrons into the light-emitting layer and the anode injects holes into the light-emitting layer. When the electrons recombine with the holes in the light-emitting layer and excitons are formed. Recombination of electron and hole results in emission.

Depending on the spin states of the hole and electron, the exciton which results from hole and electron recombination can have either a triplet or singlet spin state. Luminescence from a singlet exciton results in fluorescence whereas luminescence from a triplet exciton results in phosphorescence. The emissive efficiency of phosphorescence is three times that of fluorescence. Therefore, it is crucial to develop highly efficient phosphorescent material, in order to increase the emissive efficiency of the OLED.

Certain organometallic complexes have been reported as having intense phosphorescence (Lamansky, et al., Inorganic Chemistry, 2001, 40, 1704), and efficient OLEDs emitting in the green to red spectrum have been prepared with these complexes (Lamansky, et al., J. Am. Chem. Soc., 2001, 123, 4304). U.S. Patent Application Publication 2003/0072964A1 discloses a phosphorescent organometallic complex including phenylquinolinato ligands. Other emissive organometallic complexes can be found in U.S. Patent Application Publication 20020024293A1, 20020182441A1, 20030116788A1 and 20040102632A1.

U.S. Pat. No. 6,465,115 discloses a compound used as light-emitting layer material having the structure:

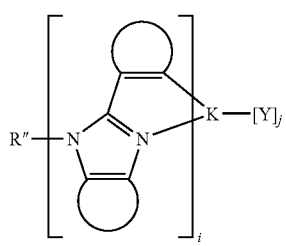

wherein K is Ir or Pt, R'' is alkyl group, Y is acetylacetonate, picolinate, or dipivaloylmetanate, and i and j are integer of 0 to 6, respectively.

While effective red or blue light-emitting organometallic complexes have been developed, more effort in development of organometallic complexes emitting green light is required.

SUMMARY

Embodiments of the invention provide organometallic compounds have the structure represented by formula (I):

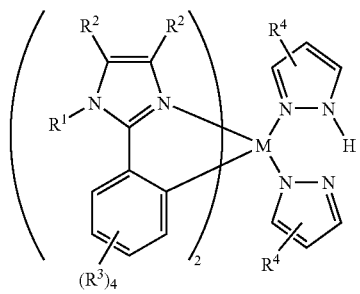

or formula (II):

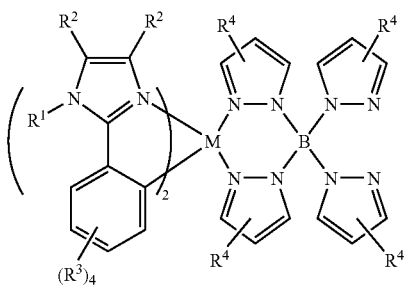

Accordingly, M can be a transition metal; $R^1$ can be hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, or $C_{3-20}$ cycloalkyl group; $R^2$ can be the same or different and is H, $C_{1-18}$ alkyl group, $C_{1-18}$ alkoxy group, $C_{3-18}$ heteroalkyl group, $C_{3-20}$ aryl group, $C_{3-20}$ heteroaryl group, or $C_{3-20}$ cycloalkyl group, or two $R^2$ groups linked together with the carbon atoms to which they are attached to form a 4- to 14-member aromatic or heteroaromatic ring; $R^3$ can be the same or different and is H, CN, tricyanovinyl, halogen, $CX_3$, $C_{1-18}$ alkyl, $C_{1-18}$ alkoxy group, $C_{3-18}$ heteroalkyl group, $C_{3-20}$ aryl group, $C_{3-20}$ heteroaryl group, or $C_{3-20}$ cycloalkyl group, wherein X is halogen, and $R^4$ can be the same or different and is H, $C_{1-3}$ alkyl group, $C_{1-3}$ alkoxy group, or $C_{1-3}$ alkyl group substituted with F, Cl, or Br.

Further provided is a display device, such as organic electroluminescent device, comprising an anode, a cathode, and organic electroluminescent layers therebetween, wherein the electroluminescent layers comprise the organometallic compound according to formula (I) or (II).

A detailed description is given in the following with reference to the accompanying drawing.

BRIEF DESCRIPTION OF THE DRAWINGS

The invention can be more fully understood by reading the subsequent detailed description in conjunction with the examples and references made to the accompanying drawing, wherein.

DETAILED DESCRIPTION

Figure 1:
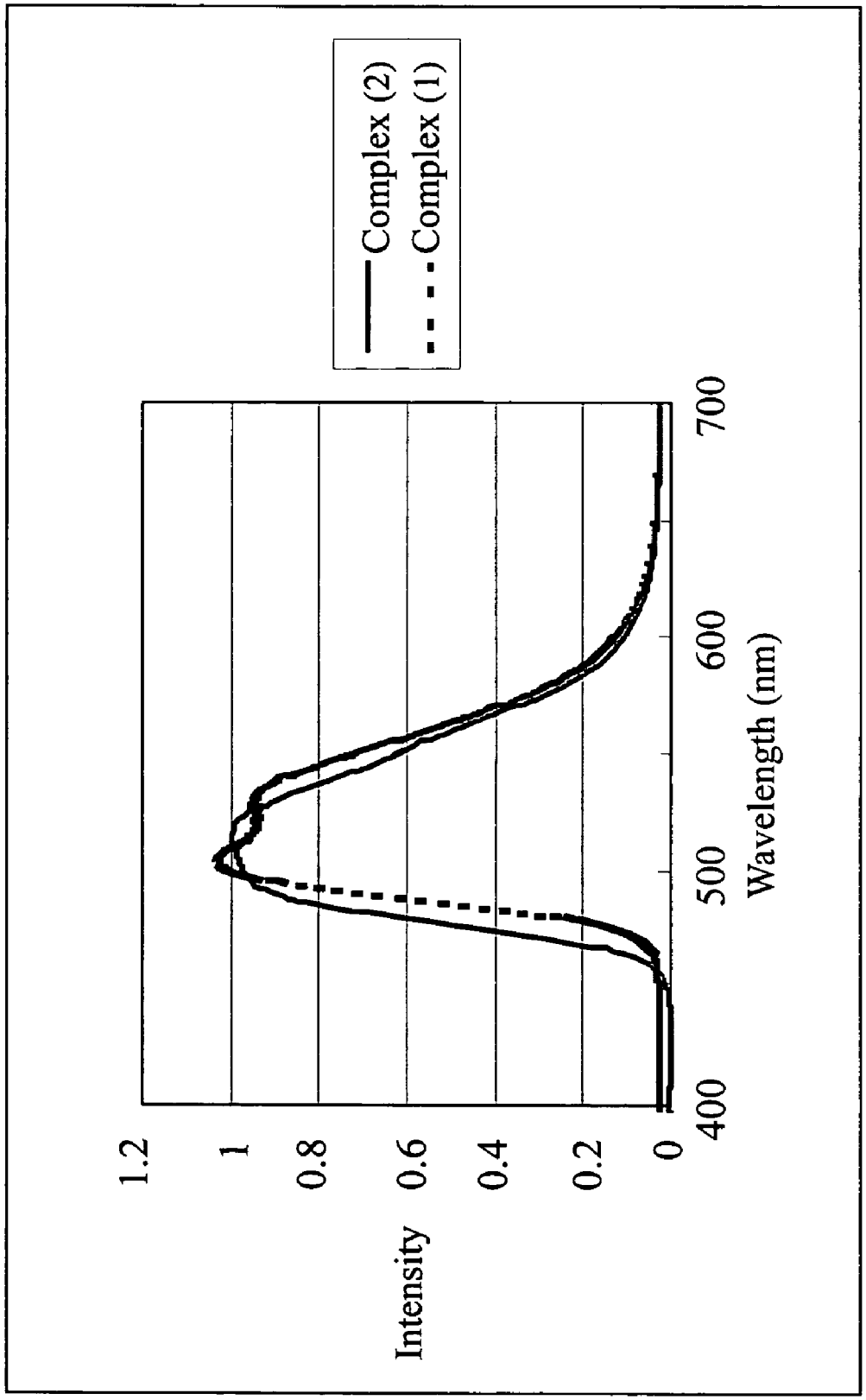
FIG. 1 is a photoluminescence spectrum plotting wavelengths against intensity of embodiments of organometallic compounds (1) and (2).

The present invention provides an organometallic complex containing an imidazole ligand and a tetrakis(1-pyrazolyl) borate ligand, or bispyrazolyl ligand, having formula (I)

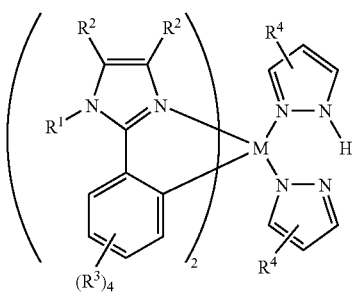

or formula (II):

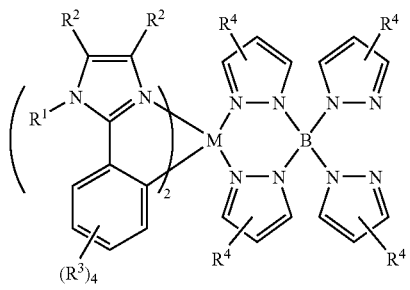

Accordingly, M can be a transition metal; $R^1$ can be hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, or $C_{3-20}$ cycloalkyl group.

$R^2$ can be the same or different and is H, $C_{1-18}$ alkyl group, $C_{1-18}$ alkoxy group, $C_{3-18}$ heteroalkyl group, $C_{3-20}$ aryl group, $C_{3-20}$ heteroaryl group, or $C_{3-20}$ cycloalkyl group, or two $R^2$ groups linked together with the carbon atoms to which they are attached to form a 4- to 14-member aromatic or heteroaromatic ring.

$R^3$ can be the same or different and is H, CN, tricyanovinyl, halogen, $CX_3$, $C_{1-18}$ alkyl, $C_{1-18}$ alkoxy group, $C_{3-18}$ heteroalkyl group, $C_{3-20}$ aryl group, $C_{3-20}$ heteroaryl group, or $C_{3-20}$ cycloalkyl group, wherein X is halogen.

$R^4$ can be the same or different and is H, $C_{1-3}$ alkyl group, $C_{1-3}$ alkoxy group, or $C_{1-3}$ alkyl group substituted with F, Cl, or Br.

Moreover, the organometallic compounds having the structure showing in formula (I) or (II) can be

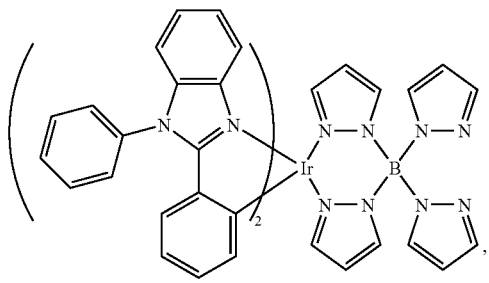

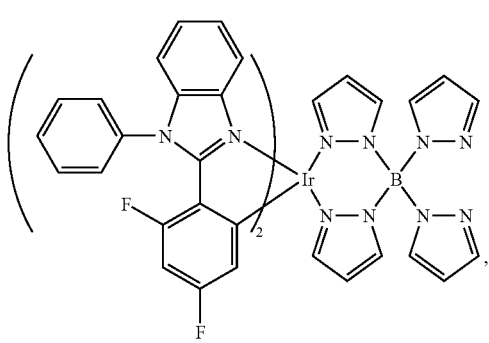

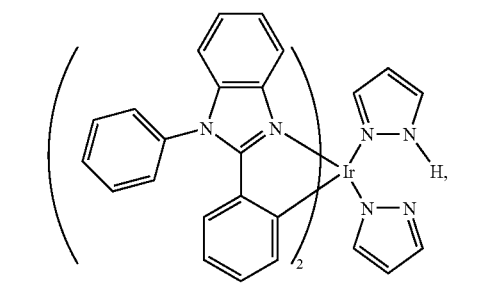

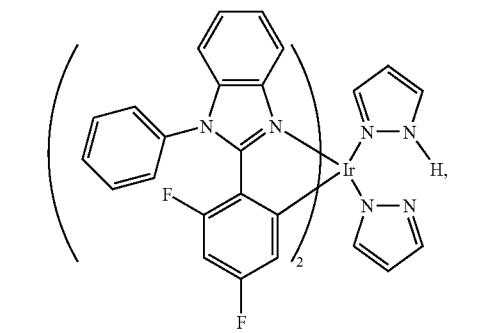

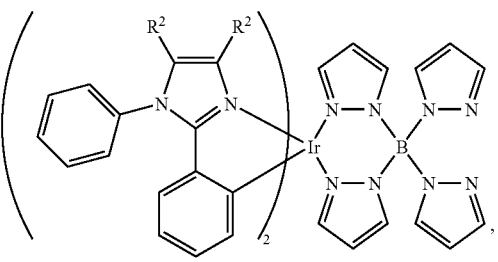

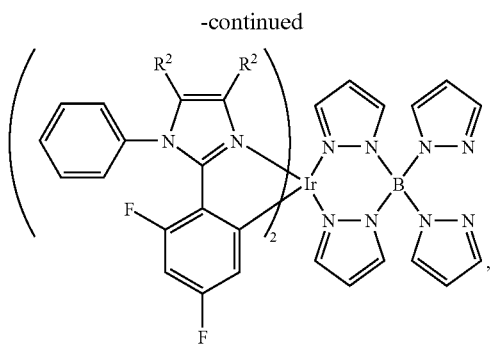

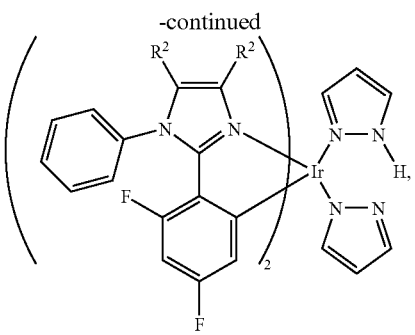

wherein $R^2$ is independently methyl, iso-butyl, or methoxy, and at least one hydrogen atom bonded to the carbon atom of the above organometallic compound can be substituted optionally by $C_{1-10}$ alkyl group, $C_{1-10}$ alkoxy group, phenyl group, or halogen.

The following examples are intended to illustrate the invention more fully without limiting their scope, since numerous modifications and variations will be apparent to those skilled in this art.

EXAMPLE 1

Organometallic Compound (1): Iridium(III) bis[1,2-diphenyl-1H-benzoimidazole] (tetrakis(1-pyrazolyl) borate)

The synthesis pathway is as follows.

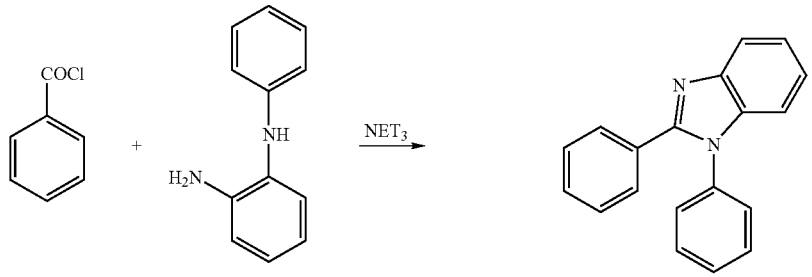

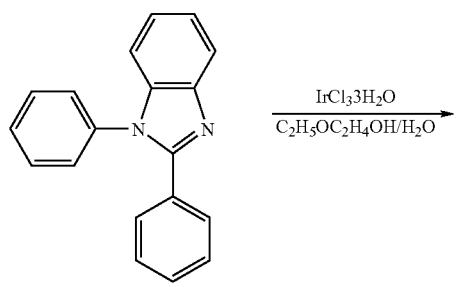

-continued

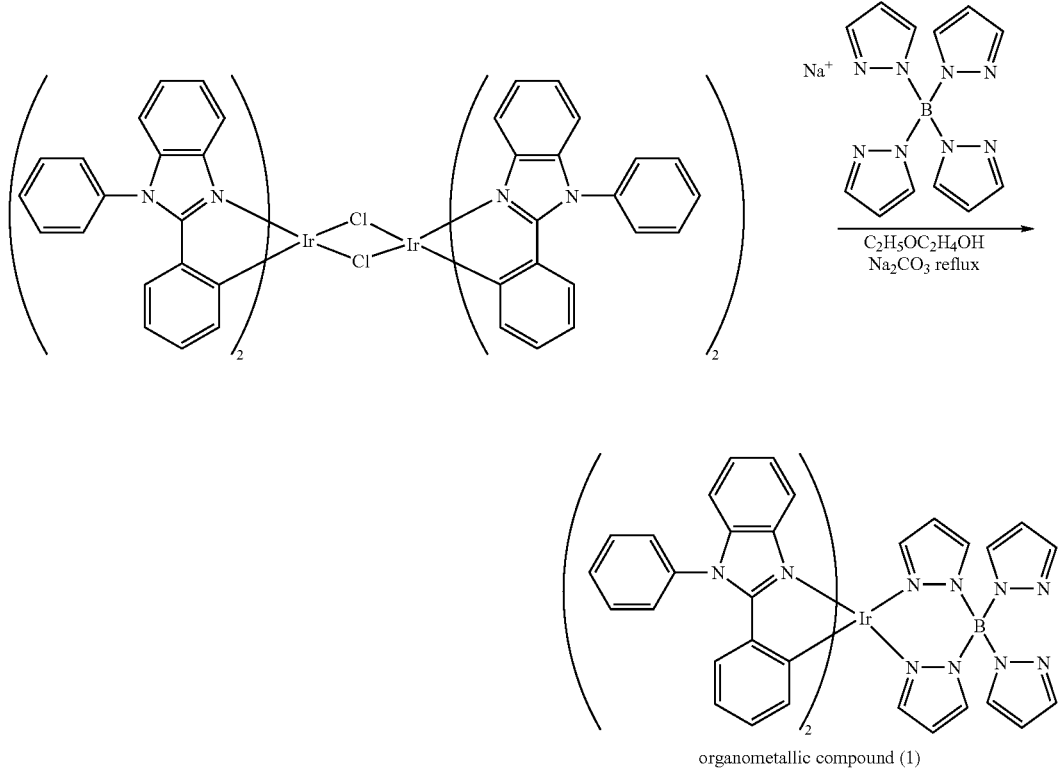

organometallic compound (1)

40 ml of N-phenyl-1,2-phenylenediamine (7.36 g, 40 mmol) was charged in a 250 ml round bottle, 10 ml of triethylamine was then added, and the mixture was cooled to 0° C. Benzoyl chloride (5.6 g, 40 mmol) was dissolved in 40 ml of dichloromethane and then slowly added to the 250 ml round bottle. The reaction was conducted under a nitrogen atmosphere for 6 hours. After the reaction was complete, ether was added to form precipitate. The solid product was collected by filtration, washed with ether several times, and heated under reduced pressure to form 1,2-diphenyl-1H-benzoimidazole (yield=7.56 g, 70%).

1,2-diphenyl-1H-benzoimidazole (6.75 g, 25 mmol) and iridium(III) chloride trihydrate (4.2 g, 12 mmol) were mixed and a mixed solution containing 60 ml of ethyoxyethanol and 20 ml of water was added. The mixture was heated to reflux under a nitrogen atmosphere for 12 hours and cooled to form yellow precipitate. The precipitate was washed with D.I. water and hexane several times to give iridium dichloro-bridged dimer (7.35 g, 4.8 mmol).

The iridium dichloro-bridged dimer (7.35 g, 4.8 mmol) and sodium tetrakis(1-pyrazolyl) borate (3.02 g, 10 mmol) were added to 60 ml of ethyoxyethanol. The mixture was heated to reflux under a nitrogen atmosphere for 12 hours. After cooling to room temperature, the solid was collected by filtration, and washed with D.I. water several times, followed by several rinses with ethanol followed by hexane to give iridium(III) bis[(1,2-diphenyl)-1H-benzoimidazole](tetrakis(1-pyrazolyl) borate) (5.04 g, 5 mmol) (organometallic compound 1). The final product was purified by vacuum sublimation.

EXAMPLE 2

Organometallic Compound (2): Iridium(III) bis[2-(2, 4-difluoro-phenyl)-1-phenyl-1H-benzoimidazole] (tetrakis(1-pyrazolyl)borate)

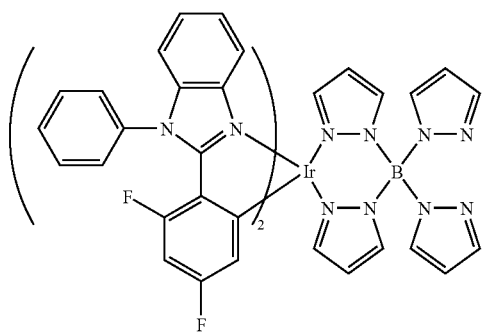

Organometallic compound (2)

N-phenyl-1,2-phenylenediamine (1.84 g, 10 mmol) and 40 ml of dichloromethane were charged in a 250 ml round bottle, 3 ml of triethylamine was added, and the mixture was cooled to 0° C. 2,4-Difluoro-benzoyl chloride (1.94 g, 11 mmol) was dissolved in 40 ml of dichloromethane and then slowly added to the 250 ml round bottle. The reaction was conducted under a nitrogen atmosphere for 6 hours. After the reaction was complete, ether was added to form precipitate. The solid product was collected by filtration, washed with ether several times, and heated under reduced pressure to form 2-(2,4-difluoro-phenyl)-1-phenyl-1H-benzoimidazole (yield=1.83 g, 60%).

2-(2,4-difluoro-phenyl)-1-phenyl-1H-benzo-imidazole (1.83 g, 6 mmol) and iridium(III) chloride trihydrate (1.1 g, 3 mmol) were mixed and then a mixed solution containing 30 ml of ethyoxyethanol and 10 ml of water was added. The mixture was heated to reflux under a nitrogen atmosphere for 12 hours and then cooled to form yellow precipitate. The precipitate was washed with D.I. water and hexane several times to give iridium dichloro-bridged dimer (2.01 g, 1.2 mmol).

The iridium dichloro-bridged dimer (2.01 g, 1.2 mmol) and sodium tetrakis(l-pyrazolyl) borate (0.91 g, 3 mmol) were added to 30 ml of ethyoxyethanol. The mixture was heated to reflux under a nitrogen atmosphere for 12 hours. After cooling to room temperature, the solid was collected by filtration, and washed with D.I. water several times, followed by several rinses with ethanol followed by hexane to give iridium(III) bis[2-(2,4-difluoro-phenyl)-1-phenyl-1H-benzoimidazole](tetrakis(1-pyrazolyl)borate)(1.08 g, 1 mmol) (organometallic compound 2). The final product was purified by vacuum sublimation.

EXAMPLE 3

Organometallic Compound (III): Iridium(III) bis[1,2-diphenyl-1H-benzoimidazole]bis(1-pyrazole)

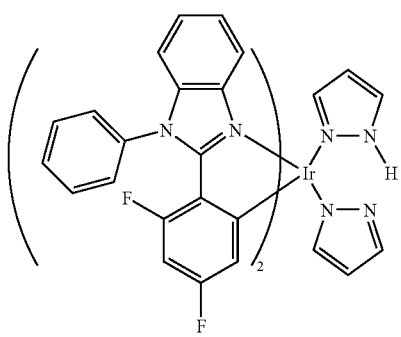

organometallic compound (3)

Example 2 was performed as Example 1 except for substitution of sodium carbonate (10 mmol) and pyrazole (10 mmol) for sodium tetrakis(1-pyrazolyl)borate (10 mmol). After purification, organometallic compound (3) was obtained.

EXAMPLE 4

Organometallic Compound (IV): Iridium(III) bis[2-(2,4-difluoro-phenyl)-1-phenyl-1H-benzoimidazole] (bis(1-pyrazole)

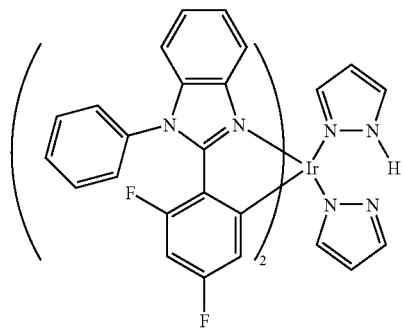

organometallic compound (3)

Example 2 was performed as Example 1 except for substitution of sodium carbonate (3 mmol) and pyrazol (3 mmol) for sodium tetrakis(1-pyrazolyl)borate (10 mmol). After purification, organometallic compound (4) was obtained.

FIG. 1 illustrates the photoluminescent spectrum of both organometallic compounds (1) and (2). For compound (1), there is no substituent on the benzene ring connecting imidazole ring and Ir. It can be seen from the spectrum of compound (1) that the light emission maximum wavelength is 515 nm. When the benzene ring is substituted with F (an electron-withdrawing group) in the para and meta positions as compound (2), there is a blue shift to 506 nm.

The organometallic compounds according to formula (I) or (II) exhibit photoluminescent and electroluminescent properties. Organic electroluminescent devices employing the organometallic compounds, acting as host materials, emit light with high luminescent efficiency under bias voltage. Furthermore, the organometallic compounds according to formula (I) or (II) can also serve as green phosphorescent dopant material for organic electroluminescent devices.

While the invention has been described by way of example and in terms of preferred embodiment, it is to be understood that the invention is not limited thereto. It is therefore intended that the following claims be interpreted as covering all such alteration and modifications as fall within the true spirit and scope of the invention.

What is claimed is:
1. An organometallic compound having a formula of:

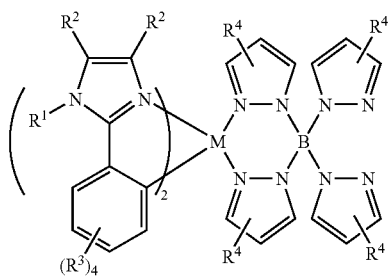

wherein

M is a transition metal;

$R^1$ is hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, or $C_{3-20}$ cycloalkyl group;

$R^2$ is independently $C_{1-18}$ alkoxy group, $C_{3-18}$ heteroalkyl group, $C_{3-20}$ aryl group, $C_{3-20}$ heteroaryl group, or $C_{3-20}$ cycloalkyl group;

$R^3$ is independently H, CN, tricyanovinyl, halogen, $CX_3$, $C_{1-18}$ alkyl, $C_{1-18}$ alkoxy group, $C_{3-18}$ heteroalkyl group, $C_{3-20}$ aryl group, $C_{3-20}$ heteroaryl group, or $C_{3-20}$ cycloalkyl group, wherein X is halogen; and $R^4$ is independently $C_{1-3}$ alkyl group, $C_{1-3}$ alkoxy group, or $C_{1-3}$ alkyl group substituted with F, Cl, or Br.

2. The organometallic compound as claimed in claim 1, wherein M is Ir, Pt, Os, Re, Ru, or Rh.

3. A display device, comprising a light-emitting layer having the organometallic compound as claimed in claim 1.

4. The display device as claimed in claim 3, wherein the organometallic compound serves as green phosphorescent dopant material.

5. A display device, comprising:

a substrate;

an anode formed on the substrate;

an organic electroluminescent layer formed on the anode; and a cathode formed on the organic electroluminescent layer, wherein, the organic electroluminescent layer comprises an organometallic compound having a formula of:

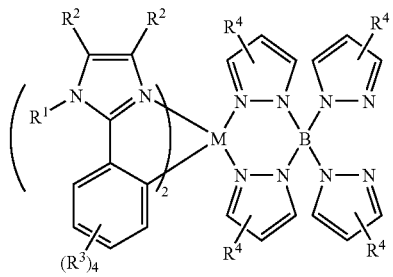

wherein

M is a transition metal;

$R^1$ is hydrogen, halogen, $C_{1-18}$ alkyl group, $C_{1-18}$ alkoxy group, $C_{3-18}$ heteroalkyl group, $C_{3-20}$ aryl group, $C_{3-20}$ heteroaryl group, or $C_{3-20}$ cycloalkyl group;

$R^2$ is independently $C_{1-18}$ alkoxy group, $C_{3-18}$ heteroalkyl group, $C_{3-20}$ aryl group, $C_{3-20}$ heteroaryl group, or $C_{3-20}$ cycloalkyl group;

$R^3$ is independently H, CN, tricyanovinyl, halogen, $CX_3$, $C_{1-18}$ alkyl, $C_{1-18}$ alkoxy group, $C_{3-18}$ heteroalkyl group, $C_{3-20}$ aryl group, $C_{3-20}$ heteroaryl group, or $C_{3-20}$ cycloalkyl group, wherein X is halogen; and $R^4$ is independently $C_{1-3}$ alkyl group, $C_{1-3}$ alkoxy group, or $C_{1-3}$ alkyl group substituted with F, Cl, or Br.

6. The device as claimed in claim 5, wherein M is Ir, Pt, Os, Re, Ru, or Rh.

7. An organometallic compound having a formula of:

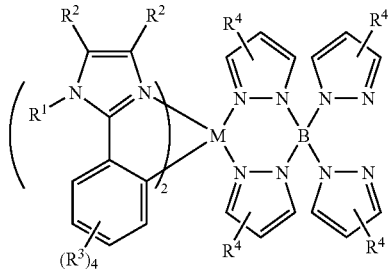

wherein

M is a transition metal;

$R^1$ is halogen, $C_{3-18}$ heteroalkyl group, or $C_{3-20}$ cycloalkyl group;

$R^2$ is independently $C_{1-18}$ alkoxy group, $C_{3-18}$ heteroalkyl group, $C_{3-20}$ aryl group, $C_{3-20}$ heteroaryl group, or $C_{3-20}$ cycloalkyl group;

$R^3$ is independently CN, tricyanovinyl, $CX_3$, $C_{3-18}$ heteroalkyl group, $C_{3-20}$ aryl group, or $C_{3-20}$ cycloalkyl group, wherein X is halogen; and $R^4$ is hydrogen.

8. The organometallic compound as claimed in claim 7, wherein M is Ir, Pt, Os, Re, Ru, or Rh.

9. A display device, comprising:

a substrate;

an anode formed on the substrate;

an organic electroluminescent layer formed on the anode; and a cathode formed on the organic electroluminescent layer, wherein, the organic electroluminescent layer comprises an organometallic compound having a formula of:

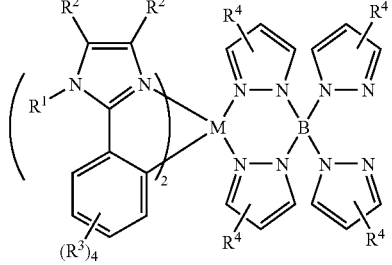

wherein

M is a transition metal;

$R^1$ is halogen, $C_{3-18}$ heteroalkyl group, or $C_{3-20}$ cycloalkyl group;

$R^2$ is independently $C_{1-18}$ alkoxy group, $C_{3-18}$ heteroalkyl group, $C_{3-20}$ aryl group, $C_{3-20}$ heteroaryl group, or $C_{3-20}$ cycloalkyl group;

$R^3$ is independently CN, tricyanovinyl, $CX_3$, $C_{3-18}$ heteroalkyl group, $C_{3-20}$ aryl group, or $C_{3-20}$ cycloalkyl group, wherein X is halogen; and $R^4$ is hydrogen.

10. The device as claimed in claim 9, wherein M is Ir, Pt, Os, Re, Ru, or Rh.

* * * * *